United States Patent
Marks et al.

(10) Patent No.: US 8,409,105 B2
(45) Date of Patent: *Apr. 2, 2013

(54) DEVICE FOR NON-INVASIVE MEASUREMENT OF BLOOD PRESSURE AND ANKLE-BRACHIAL INDEX

(75) Inventors: Lloyd A. Marks, Westfield, NJ (US); Michael Smith, Oradell, NJ (US)

(73) Assignee: Smithmarks, Inc., Westfield, NJ (US)

(*) Notice: Subject to any disclaimer, the term of this patent is extended or adjusted under 35 U.S.C. 154(b) by 752 days.

This patent is subject to a terminal disclaimer.

(21) Appl. No.: 12/564,573

(22) Filed: Sep. 22, 2009

(65) Prior Publication Data

US 2010/0241014 A1 Sep. 23, 2010

Related U.S. Application Data

(63) Continuation-in-part of application No. 11/875,355, filed on Oct. 19, 2007, now Pat. No. 7,887,491.

(51) Int. Cl.
*A61B 5/02* (2006.01)
(52) U.S. Cl. .......... 600/490; 600/485; 600/500
(58) Field of Classification Search .......... 600/485, 600/489–502
See application file for complete search history.

(56) References Cited

U.S. PATENT DOCUMENTS

| | | | |
|---|---|---|---|
| 4,343,314 A | 8/1982 | Sramek | |
| 5,447,161 A * | 9/1995 | Blazek et al. | 600/490 |
| 6,582,374 B2 | 6/2003 | Yokozeki | |
| 7,024,234 B2 | 4/2006 | Margulies et al. | |
| 7,118,534 B2 | 10/2006 | Ward et al. | |
| 2001/0012916 A1* | 8/2001 | Deuter | 600/485 |
| 2001/0037068 A1* | 11/2001 | Goto et al. | 600/485 |
| 2005/0070807 A1* | 3/2005 | Marks et al. | 600/505 |
| 2006/0247540 A1 | 11/2006 | Ide | |
| 2008/0033307 A1* | 2/2008 | Baudoin et al. | 600/490 |

OTHER PUBLICATIONS

Marks LA, "Digital Enhancement of the Admittance Plethysmogram", IEEE Transactions on Biomedical Engineering, vol. BME-34, No. 3, Mar. 1987.

* cited by examiner

*Primary Examiner* — Patricia Mallari
*Assistant Examiner* — Christian Jang
(74) *Attorney, Agent, or Firm* — Blank Rome LLP

(57) ABSTRACT

A device for non-invasive measurement of blood pressure includes a blood pressure cuff, a plethysmographic electrode for acquiring an impedance plethysmogram distal to the cuff and a processing device to inflate and deflate the cuff, generate the impedance plethysmogram and to determine the systolic and diastolic blood pressures. It is determined when the cuff is completely occluding the extremity, e.g., by detecting pulses at a second, partially occluded cuff or by a photoplethysmogram attached to the big toe. The device can be used to measure systolic or diastolic blood pressure or both. It can also be used to take ankle-brachial measurements. An autocorrelation technique can be used to correct noise.

35 Claims, 4 Drawing Sheets

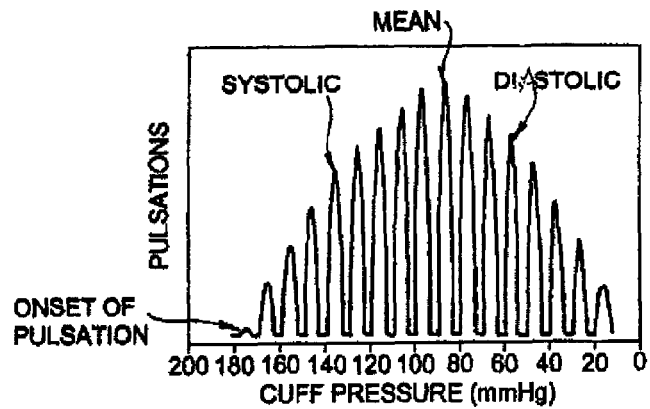
FIG. 1
(PRIOR ART)
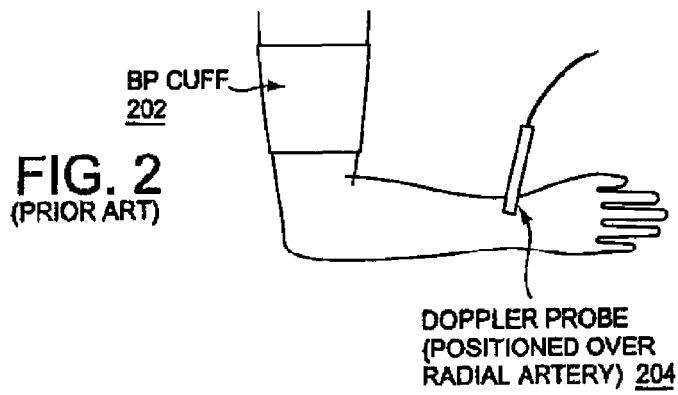
FIG. 2
(PRIOR ART)
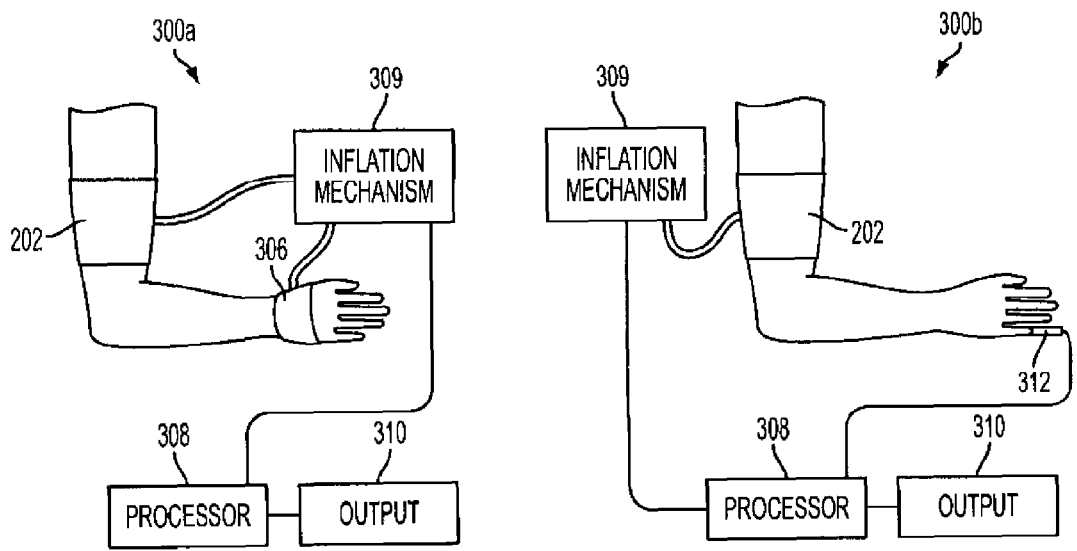
FIG. 3A          FIG. 3B

DEVICE FOR NON-INVASIVE MEASUREMENT OF BLOOD PRESSURE AND ANKLE-BRACHIAL INDEX

REFERENCE TO RELATED APPLICATION

The present application is a continuation-in-part of U.S. patent application Ser. No. 11/875,355, filed Oct. 19, 2007, now U.S. Pat. No. 7,887,491, whose disclosure is hereby incorporated by reference in its entirety into the present disclosure.

FIELD OF THE INVENTION

The present invention is directed to a system and method for non-invasive measurement of blood pressure and more particularly to such a system and method using plethysmography.

DESCRIPTION OF RELATED ART

Non-invasive blood pressure (NIBP) machines work by monitoring cuff pressure as a blood pressure cuff is being deflated (after it has been inflated to a pressure that is sufficiently higher than systolic pressure to stop all pulsations in the cuff) and applying a mathematical algorithm to the cuff pressure waveforms. When the cuff is significantly above systolic blood pressure, there are no pulsations. When the cuff pressure has been deflated to some value significantly above systolic pressure, pulsations appear. As the cuff is deflated, the pulsations increase in magnitude and reach a maximum when the cuff is inflated to the mean blood pressure. Then the pulsations decrease in magnitude as the cuff is further deflated and persist below diastolic blood pressure. The pulsations are small waveforms which "ride" on the decreasing inflation pressure. They are extracted by high pass filtering and appear somewhat like the plot in FIG. 1. Note that the onset of pulsations does not correspond to systolic pressure and the termination of pulsations does not correspond to diastolic pressure. These values are derived from a mathematical algorithm (differing from manufacturer to manufacturer) that uses the cuff pressure at the points of onset of pulsations, maximum impulse, and termination of the pulsations as input data. Not surprisingly, these measurements can be quite inaccurate when compared with "gold-standard" invasive BP measurements.

When an accurate systolic blood pressure measurement is required, as when making Ankle-Brachial-Index (ABI) measurements (the ratio of ankle systolic pressure to brachial systolic pressure), the systolic pressure determined by NIBP machines is generally considered not accurate enough. Instead, the more accurate "Doppler Systolic Method" is used, as shown in FIG. 2. With this method, the pulse is monitored distal to the cuff 202 with a Doppler ultrasound device 204. As the cuff is deflated, the Doppler sounds appear when the cuff is deflated to systolic pressure. As the Doppler provides a direct indication of flow distal to the cuff, this technique provides a reliable, accurate and reproducible measurement of systolic pressure. The Doppler pulsations do not disappear with further cuff deflation, so this technique is not useful for measuring diastolic pressure.

The Doppler technique requires application of ultrasound gel, searching for and finding the pulse, and continuous monitoring of the pulse while the cuff is deflated. This requires a skilled technician and can be tedious, messy and time consuming. Furthermore, it does not provide a measurement of diastolic pressure.

Various plethysmographic techniques are disclosed in U.S. Published Patent Application No. 2006/0247540 to Ide, U.S. Pat. No. 4,343,314 to Sramek, U.S. Pat. No. 6,482,374 to Yokozeki and U.S. Pat. No. 7,118,534 to Ward et al. However, they do not adequately account for noise.

In a separate field of endeavor, U.S. Pat. No. 7,024,234 to Margulies et al teaches the use of a photoplethysmogram on an extremity (e.g., finger or big toe) to measure the slope of a blood pressure waveform in order to monitor the patient's autonomic nervous system. However, that reference does not teach a way to resolve the above-noted problems.

SUMMARY OF THE INVENTION

It is therefore an object of the invention to provide a system and method for accurately measuring systolic or diastolic blood pressure that it based upon the measurement of flow distal to the cuff, can be performed easily and reliably by an unskilled individual, does not require application of gel, is not time consuming, is resistant to noise, and provides the measurement in an automated fashion.

To achieve the above and other objects, the present invention is directed to a device including a blood pressure cuff, a plethysmographic device for acquiring a plethysmogram distal to the cuff (impedance, optical, or another device such as a strain gauge plethysmograph) and a processing device to inflate and deflate the cuff, generate the plethysmogram and to determine the systolic and diastolic blood pressures. The device can be used to measure systolic or diastolic blood pressure or both, although in a preferred embodiment it measures systolic blood pressure. It can also be used to take ankle-brachial measurements. A photoplethysmogram is attached to a location such as a big toe to determine when the cuff is completely occluding the extremity. That determination can be made by alternate means; for example, pulses can be taken in a partially occluded cuff on the foot to determine when the ankle cuff is achieving complete occlusion. The invention is further directed to the corresponding method.

The invention can be adapted to human and non-human animal patients. In the latter case, the invention can be used on a limb or tail of the patient.

Noise can be compensated for by a type of auto-correlation technique. First, the onset of electrical activity (the QRS complex) for each cardiac cycle is identified. Successive impedance waveforms are captured using the QRS as a gating signal. These waveforms are then high pass filtered such that there is an equal area above and below the baseline. Corresponding points (i.e., equidistant in time from the QRS complex) on an even number of successive waves are multiplied, producing a "product waveform" that consists of a discrete point for each of the multiplications. Then, the products can be summed.

BRIEF DESCRIPTION OF THE DRAWINGS

A preferred embodiment of the present invention will be disclosed in detail with reference to the drawings, in which:

FIG. 1 shows a high-pass-filtered waveform taken by deflating a blood pressure cuff;

FIG. 2 shows a conventional Doppler method for determining systolic pressure;

FIGS. 3A and 3B show a device according to two variations of the preferred embodiment used on a patient's foot;

DETAILED DESCRIPTION OF THE PREFERRED EMBODIMENT

Figure 3C:
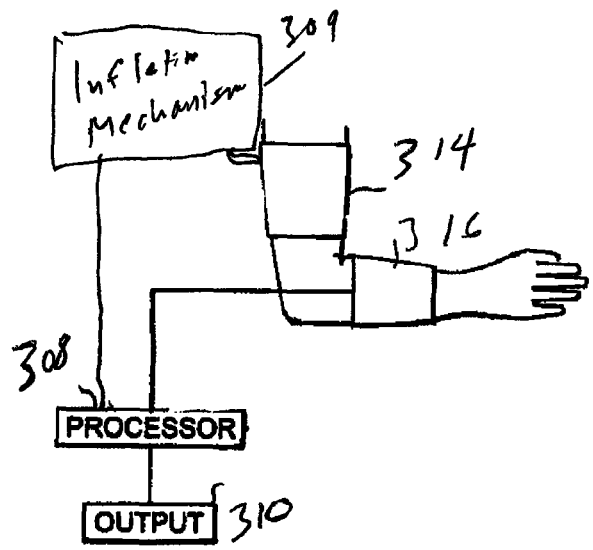
FIG. 3C shows another variation of the preferred embodiment on a patient's arm.

A preferred embodiment of the present invention will be set forth in detail with reference to the drawings, in which like reference numerals refer to like elements or method steps throughout.

As shown in FIG. 3A, the device 300a according to one variation of the preferred embodiment includes a conventional blood pressure cuff 202 on the patient's ankle and a partially occluded cuff 306 on the foot, a processing device 308 for controlling the inflation and deflation of the cuff 202, an inflation mechanism 309 controlled by the processor 308 and an output 310 (such as a display) for outputting the results. The device 300b of FIG. 3B differs from the device 300a of FIG. 3A in that the partially occluded cuff 306 is replaced by a photoplethysmogram sensor 312 on a patient's toe. In either of those variations of the preferred embodiment, the processing device 308 can take signals from the partially occluded cuff 306 or the photoplethysmogram sensor 312 to determine when the cuff 202 is fully occluding as part of the measurement process. Inflation mechanisms usable in the preferred embodiment are well known in the art and will therefore not be described in detail here; however, their use in the context of the present invention is believed to be novel.

The device of FIG. 3A or 3B can be modified as shown in FIG. 3C on the patient's arm. In this variation, occluding cuff 314 is applied to the upper arm and an impedance sensor electrode 316 is applied to the forearm. The cuff is inflated by an inflation mechanism 309 that is controlled by the processor.

The variations shown in FIGS. 3A and in 3B can be used on any extremity

Systolic pressure is determined in the following manner. There is no flow distal to the cuff when it is inflated above systolic pressure, and a pulse (reflected as a change in the impedance waveform or optical plethysmogram) will appear when the cuff is deflated below systolic pressure.

Figure 4:
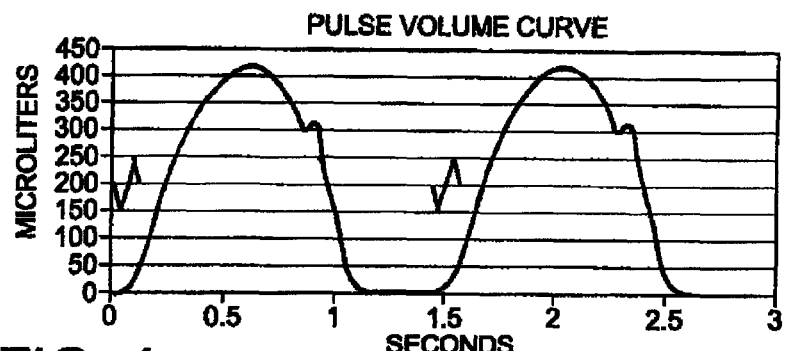
FIG. 4 shows noise-free pulse volume waveforms.
Figure 5:
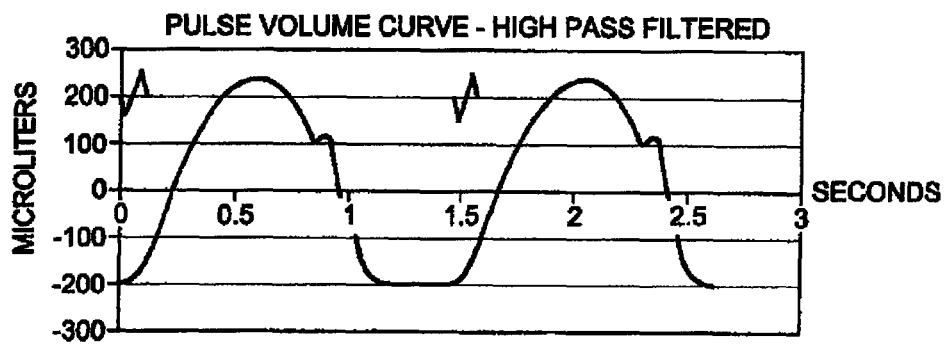
FIG. 5 shows high-pass-filtered pulse volume waveforms.
Figure 6:
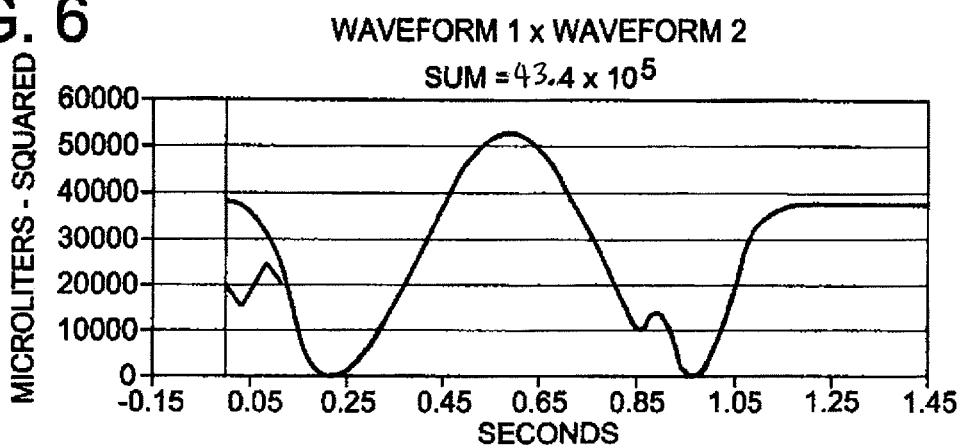
FIG. 6 shows a result of multiplication of two high-pass-filtered pulse volume waveforms such as those of FIG. 5.

Because the impedance plethysmogram is a small signal which may be partially obscured or hidden by noise, signal processing techniques are used to identify and/or extract the pulse volume wave. This is done by a type of auto-correlation technique. First, the onset of electrical activity (the QRS complex) for each cardiac cycle is identified. Successive impedance waveforms are captured using the QRS as a gating signal (FIG. 4). These waveforms are then high pass filtered such that there is an equal area above and below the baseline (FIG. 5). Corresponding points (i.e., equidistant in time from the QRS complex) on an even number of successive waves are multiplied, producing a "product waveform" that consists of a discrete point for each of the multiplications (FIG. 6). Then, the products can be summed.

When the cuff pressure is below systolic, successive waveforms will be similar to one another (concordant). When two concordant waveforms are multiplied, negative points are multiplied by negative points, and positive points are multiplied by positive points, resulting in a positive product at all points (FIG. 6). The sum of these multiplications will therefore be a definitive positive number (in this example, and with these units, $43.4 \times 10^5$). As the waveforms are not perfectly concordant in the real world, there may be some negative products. However, these negative products are negligible when compared to the positive products.

Figure 7:
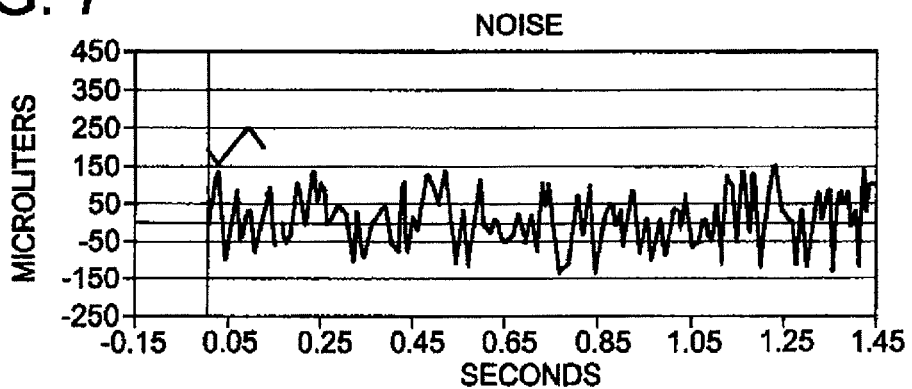
FIG. 7 shows a typical pure noise waveform.
Figure 8:
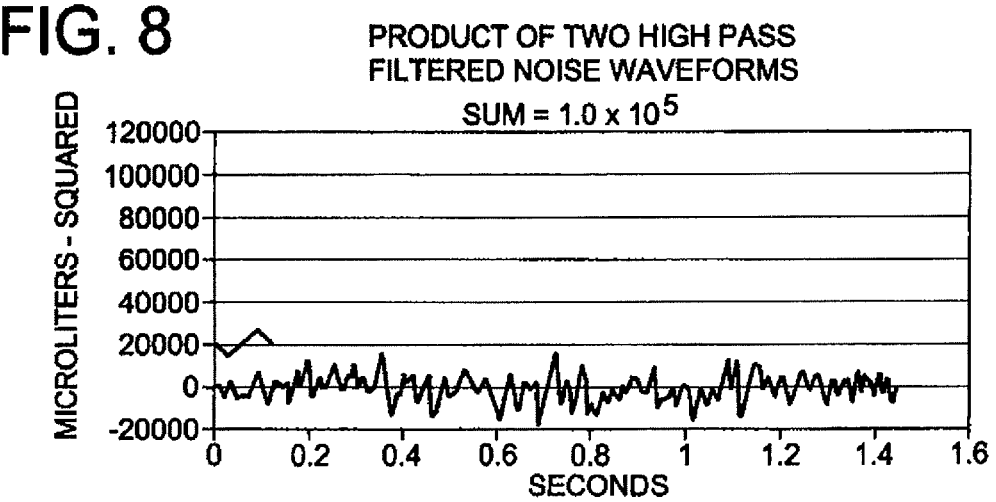
FIG. 8 shows a product of two pure noise waveforms.
Figure 9:
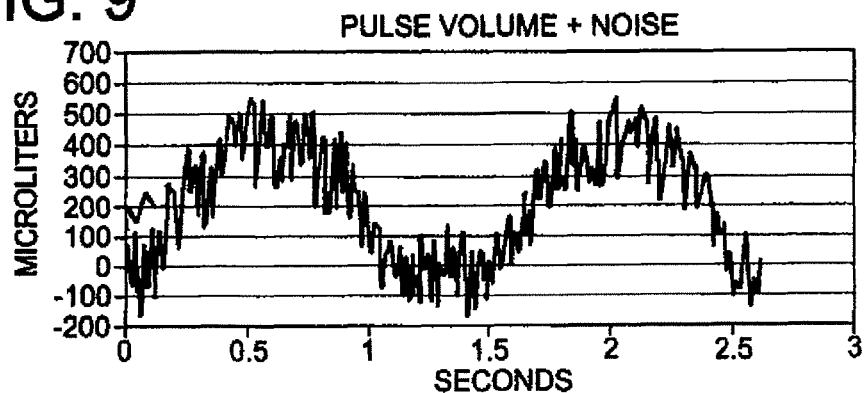
FIG. 9 shows a pulse-volume waveform that also includes noise.
Figure 10:
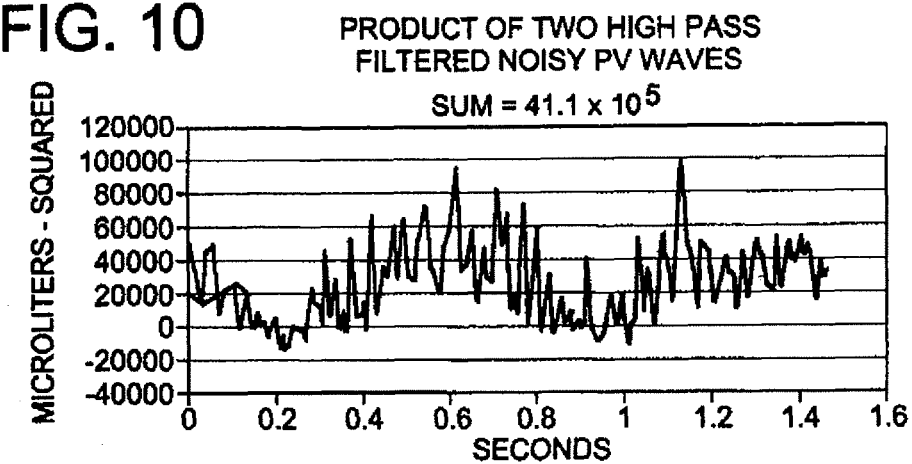
FIG. 10 shows a product of two (high pass filtered) noisy pulse volume waveforms such as those of FIG. 9.

When the cuff pressure is greater than systolic pressure, the waves will be pure noise. A typical noise waveform is shown in FIG. 7. Multiplying any waveform with a pure noise waveform will result in a series of products which are randomly both positive and negative (FIG. 8), and which, when summed, will be a small (or even possibly a negative) number when compared to the sum of products when the waveforms are concordant. In this example and with these units, the sum of products is $1.0 \times 10^5$. In the "real world," the pulse volume wave-forms contain both signal and noise (FIG. 9). The product of two such high-pass-filtered "real world" wave-forms is shown in FIG. 10. In this example, and with these units, the sum of products is $41.4 \times 10^5$. This is reasonably close to the sum of products of the ideal waveforms, and easily distinguishable from the sum of products of the noise waveforms. By multiplying four waveforms (instead of two), the chance of random concordance between noise waveforms is minimized. We have found this method to provide accurate detection of the systolic pressure when compared with the traditional auscultatory or doppler methods.

To automate the process of determining systolic pressure, the processor 308 controls the inflation mechanism 309 to inflate the cuff 202 either to a predetermined fixed pressure (e.g. 200 mmHg) or some adaptively determined pressure (e.g. 20 mmHg past when there is no longer a discernable concordant pulse wave) and then slowly (e.g. 2 mm Hg per second) deflates the cuff. During the deflation, the computer calculates the products of groups of four successive waves. The arm should be relatively stationary during this process. An indication such as providing a visual output of the PV waveform or producing a sound that is reflective of the PV waveform may be provided to the operator of the device to let the operator know if the patient's limb is relatively motionless and producing a good PV waveform. When the 4 beat multiplication method is used, systolic pressure is identified as occurring 4 beats before concordance is first detected (i.e. when the multiplied waveform and/or the sum of products is greater than a suitable threshold value). The threshold may be a fixed value or may be adaptively determined as a function of the corresponding values obtained as the cuff is being inflated (e.g. a fixed percentage of the maximum value obtained during inflation). To improve accuracy, the processor can hold the estimated systolic pressure for a period of time, looking for concordant wave-forms and inflate and deflate the cuff above and below that point until a consistent result is obtained, by iteration. One scheme involves an initial bleed rate that is relatively fast (e.g. 5 mmHg/sec) used to provide a first estimate of systolic pressure. The cuff is then inflated a fixed amount (e.g. 10 mmHg) above the first estimate of the systolic BP. Then a slow bleed (e.g. 2 mmHg is performed to obtain a second, more accurate measurement of systolic BP.

Figure 11:
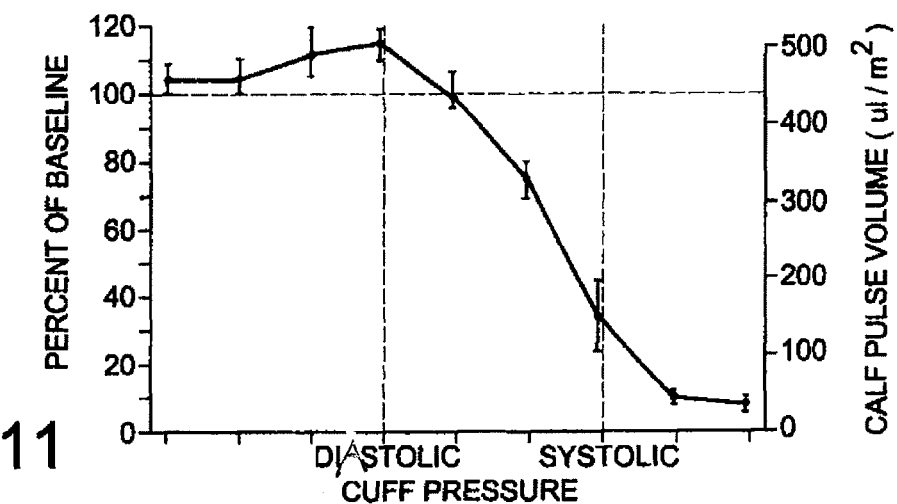
FIG. 11 shows pulse volume as a function of cuff pressure when diastolic pressure is measured.

Diastolic pressure is determined in the following manner. In contrast to the Doppler method, the method described in this disclosure can also be used to determine diastolic pressure. Pulse volume is maximum when a proximal cuff is inflated to diastolic pressure (see "Digital Enhancement of the Admittance Plethysmogram," Marks L A, IEEE Transactions on Biomedical Engineering, Vol. BME-34, No. 3, March 1987). This effect is shown in FIG. 11, which is reproduced from that paper. Therefore, as the cuff is deflated, the sum of the products of corresponding waveform points will increase in amplitude until the cuff reaches diastolic pressure. After that point, the sum of products will decrease. The difference between successive sums of products will be negative as long as the cuff is being deflated between systolic and diastolic pressure. After the cuff falls below diastolic pressure, this difference will be positive. The computer can seek out the point at which the sum of products is at its maximum and confirm its accuracy through iteration in much the same way that it determines systolic pressure, as described above.

Selective Signal Averaging is another method that can be used to implement this invention. In this case, the cuff is held at a series of fixed pressures while averaging takes place. The averaged waveform will be flat and without pulsations when the cuff is above systolic pressure and will have non-zero pulsations when the cuff is below systolic pressure. The pulse amplitude will be at its maximum when the cuff is at diastolic pressure. These points can be determined by a suitable computational device. It may be possible to perform an estimate of BP using the raw waveform, i.e., without using either multiplication or averaging. However, the accuracy would probably be much less.

This device can be used to obtain the systolic blood pressure in the arm and in the ankles in order to calculate the ankle-brachial index. In the case of the arm, the cuff is placed on the upper arm and the impedance electrodes on the forearm. For the ankle, the occluding cuff is placed on the ankle, and an impedance electrode (or photoplethysmogram sensors or a partially inflated cuff) is placed on the foot. Because the systolic pressure is identified by the presence or absence of a concordant pulse, it is not necessary to compute the pulse volume in the foot for this technique. This means that a bipolar (rather than quadripolar) impedance electrode (or the pressure pulsations in a partially occluded cuff or the pulse generated by a photoplethysmogram) can be used to detect the pulse. None of these methods provides a quantifiable physiologic measurement of the pulse, but this is not necessary as they must only detect the presence or absence of the pulse and not its amplitude. When using one of these methods, however, baseline measurements in arbitrary rather than physiologic units must be measured before the cuff is occluded. These are used to determined the baseline multiplied waveform sums, which, in turn, are used to determine the threshold values used for determining the presence or absence of concordance. Once the systolic pressures are determined as described above, it is a straightforward matter for the computational device to calculate the ratio of the systolic pressure in the ankles to the systolic pressure in the arms, thus determining the ankle-brachial index in an automated fashion.

It may be desirable to provide a display which displays the systolic BP of the 4 extremities and the ABI's.

The above system may be combined with a system that provides 4 extremity quantitative pulse volume curves. The combination of a system that provides automated ABI measurements with a system that provides quantitative PV curves may be considered a "Vascular Disease Screening System" suitable for primary care physicians, cardiologists, podiatrists and other physicians to identify medical conditions which may require medical or surgical intervention. A computational device may be provided which can package this information in a transmittable computer file that could be sent e.g to a vascular surgeon for consultation and/or further care.

It may be desirable to provide a display which displays, for each extremity, a pulse volume curve, a systolic blood pressure, a diastolic pressure (if available), and the value of the limb's baseline impedance. Furthermore, it may be useful to provide a display of the first derivative of the PV curve, which would be the instantaneous net inflow into the limb segment.

While a preferred embodiment of the present invention has been disclosed in detail above, those skilled in the art who have reviewed the present disclosure will readily appreciate that other embodiments can be realized within the scope of the invention. For example, numerical values are illustrative rather than limiting. Also, any suitable cuff and plethysmographic device can be used. The software used to control the processor can be supplied on any suitable computer-accessible medium. Therefore, the present invention should be construed as limited only by the appended claims.

We claim:

1. A method for non-invasively measuring blood pressure of a patient, the method comprising:
    (a) attaching a pressure cuff to an extremity of the patient;
    (b) attaching a plethysmographic device to the extremity at a distal location relative to the pressure cuff;
    (c) inflating the cuff to cause occlusion in the extremity and deflating the cuff;
    (d) determining when the cuff has caused complete occlusion in step (c) by using a device for determining the complete occlusion;
    (e) taking a series of waveforms representing blood pulsations by using the plethysmographic device;
    (f) measuring the blood pressure from the waveforms in a processor by multiplying corresponding points in groups of the waveforms in the processor to produce product waveforms and measuring the blood pressure from the product waveforms; and
    (g) outputting the blood pressure measured in step (f) from the processor.

2. The method of claim 1, wherein the device for determining the complete occlusion comprises a second cuff, and wherein step (d) comprises attaching the second cuff to the extremity, partially occluding the extremity by use of the second cuff, and detecting pulses at the second cuff.

3. The method of claim 1, wherein the device for determining the complete occlusion comprising the plethysmographic device, said plethysmographic device further comprising a photoplethysmogram sensor, and wherein step (d) comprises attaching the photoplethysmogram sensor to the extremity and detecting pulses with a photoplethysmogram.

4. The method of claim 3, wherein the photoplethysmogram sensor is attached to a toe of the patient.

5. The method of claim 1, wherein the plethysmographic device comprises an impedance plethysmographic electrode.

6. The method of claim 1, wherein the groups of the waveforms are groups of even numbers of the waveforms.

7. The method of claim 6, wherein the groups of the waveforms are groups of at least four of the waveforms.

8. The method of claim 1, wherein the blood pressure comprises systolic blood pressure.

9. The method of claim 8, wherein step (f) comprises:
    (i) inflating the cuff until the waveforms include no concordant waveforms;
    (ii) deflating the cuff;
    (iii) identifying a pressure of inflation of the cuff at which the waveforms become concordant; and
    (iv) measuring the systolic blood pressure from the pressure identified in step (f)(iii).

10. The method of claim 9, wherein step (f) is performed iteratively.

11. The method of claim 8, wherein step (c) is performed twice, once with a first deflation rate and once with a second deflation rate which is slower than the first deflation rate.

12. The method of claim 8, wherein the systolic blood pressure is measured in both an arm and a leg of the patient.

13. The method of claim 12, wherein an ankle-brachial index is calculated.

14. The method of claim 13, wherein said ankle-brachial index is calculated automatically and a pulse volume curve is provided.

15. The method of claim 1, wherein the blood pressure comprises diastolic blood pressure.

16. The method of claim 15, wherein step (f) comprises:
   (i) performing a point-by-point multiplication on the waveforms to obtain multiplied waveforms; and
   (ii) determining a maximum of the multiplied waveforms.

17. The method of claim 15, wherein step (f) comprises:
   (i) performing a point-by-point multiplication on the waveforms to obtain multiplied waveforms;
   (ii) summing the multiplied waveforms to obtain a summed waveform; and
   (iii) determining a maximum of the summed waveform.

18. The method of claim 17, wherein step (f) is performed iteratively.

19. A device for non-invasively measuring blood pressure of a patient, the device comprising:
   (a) a pressure cuff for attachment to an extremity of the patient;
   (b) a plethysmographic device for attachment to the extremity at a distal location relative to the pressure cuff;
   (c) a device for determining when the cuff has caused complete occlusion;
   (d) a processor, connected to the pressure cuff and the plethysmographic device, for inflating and deflating the cuff, taking a series of waveforms representing blood pulsations by using the plethysmographic device, multiplying corresponding points in groups of the waveforms to produce product waveforms, and measuring the blood pressure from the product waveforms; and
   (e) an output for outputting the blood pressure measured by the processor.

20. The device of claim 19, wherein the device for determining comprises a second cuff for attachment to the extremity and partially occluding the extremity and a detector for detecting pulses at the second cuff.

21. The device of claim 19, wherein the device for determining comprising the plethysmographic device, said plethysmographic device further comprising a photoplethysmogram sensor for attachment to the extremity and for detecting pulses.

22. The device of claim 19, wherein the plethysmographic device comprises an impedance plethysmographic electrode.

23. The device of claim 19, wherein the groups of the waveforms are groups of even numbers of the waveforms.

24. The device of claim 23, wherein the groups of the waveforms are groups of at least four of the waveforms.

25. The device of claim 19, wherein the blood pressure comprises systolic blood pressure.

26. The device of claim 25, wherein the processor measures the systolic blood pressure by:
   (i) inflating the cuff until the waveforms include no concordant waveforms;
   (ii) deflating the cuff;
   (iii) identifying a pressure of inflation of the cuff at which the waveforms become concordant; and
   (iv) measuring the systolic blood pressure from the pressure identified in step (iii).

27. The device of claim 26, wherein the processor performs steps (i)-(iv) iteratively.

28. The device of claim 25, wherein the processor inflates and deflates the cuff twice, once with a first deflation rate and once with a second deflation rate which is slower than the first deflation rate.

29. The device of claim 25, wherein the systolic blood pressure is measured in both an arm and a leg of the patient.

30. The device of claim 29, wherein an ankle-brachial index is calculated.

31. The device of claim 30, wherein said ankle-brachial index is calculated automatically and a pulse volume curve is provided.

32. The device of claim 19, wherein the blood pressure comprises diastolic blood pressure.

33. The device of claim 32, wherein the processor measures the diastolic blood pressure by:
   (i) performing a point-by-point multiplication on the waveforms to obtain multiplied waveforms; and
   (ii) determining a maximum of the multiplied waveforms.

34. The device of claim 32, wherein the processor measures the diastolic blood pressure by:
   (i) performing a point-by-point multiplication on the waveforms to obtain multiplied waveforms;
   (ii) summing the multiplied waveforms to obtain a summed waveform; and
   (iii) determining a maximum of the summed waveform.

35. The device of claim 34, wherein the processor performs steps (i)-(iii) iteratively.

* * * * *